(12) United States Patent
Nieskens et al.

(10) Patent No.: US 10,703,689 B2
(45) Date of Patent: Jul. 7, 2020

(54) PROCESSES FOR IMPROVING THE ACTIVITY OF HYBRID CATALYSTS

(71) Applicant: Dow Global Technologies LLC, Midland, MI (US)

(72) Inventors: Davy L. S. Nieskens, NM Hoek (NL); Aysegul Ciftci Sandikci, NM Hoek (NL); Peter E. Groenendijk, NM Hoek (NL); Andrzej Malek, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/483,653

(22) PCT Filed: Feb. 2, 2018

(86) PCT No.: PCT/US2018/016617
§ 371 (c)(1),
(2) Date: Aug. 5, 2019

(87) PCT Pub. No.: WO2018/144840
PCT Pub. Date: Aug. 9, 2018

(65) Prior Publication Data
US 2020/0123078 A1    Apr. 23, 2020

Related U.S. Application Data (60) Provisional application No. 62/454,954, filed on Feb. 6, 2017.

(51) Int. Cl.
*C07C 1/04*        (2006.01)
*B01J 29/85*       (2006.01)
(Continued)

(52) U.S. Cl.
CPC .............. *C07C 1/048* (2013.01); *B01J 23/80* (2013.01); *B01J 29/85* (2013.01); *C07C 1/047* (2013.01);
(Continued)

(58) Field of Classification Search
CPC ..... C07C 1/048; C07C 1/047; C07C 2521/02; C07C 2529/85; C07C 2523/72;
(Continued)

(56) References Cited

U.S. PATENT DOCUMENTS 4,216,194 A   8/1980   Regier
4,440,871 A   4/1984   Lok et al.
(Continued)

FOREIGN PATENT DOCUMENTS

CA        1205092 A      5/1986
WO        2016007607 A1  1/2016

OTHER PUBLICATIONS

Liu et al., "Synthesis of SAPO-34 templated by diethylamine: Crystallization process and Si distribution in the crystals," Microporous and Mesoporous Materials, 114 (2008) 1-3, 416-423.
(Continued)

*Primary Examiner* — Jafar F Parsa
(74) *Attorney, Agent, or Firm* — Dinsmore & Shohl LLP (57) ABSTRACT

A process for converting a feed stream to $C_2$ to $C_5$ hydrocarbons includes introducing a feed stream of hydrogen and at least one carbon-containing component selected from CO, $CO_2$, and mixtures thereof into a reaction zone at an initial reactor pressure and an initial reactor temperature. The feed stream is contacted to a hybrid catalyst positioned in the reaction zone, and the hybrid catalyst includes a methanol synthesis component and a solid microporous acid material. The pressure within the reaction zone is increased during the contacting of the feed stream to the hybrid catalyst from the
(Continued)

initial reactor pressure to a final reactor pressure. A temperature within the reaction zone at any time during the contacting of the feed stream to the hybrid catalyst is within ±20° C. of the initial reactor temperature.

15 Claims, 2 Drawing Sheets (51) Int. Cl.
  *B01J 23/80* (2006.01)
  *C10G 2/00* (2006.01)
(52) U.S. Cl.
  CPC ............... *C10G 2/33* (2013.01); *C10G 2/50* (2013.01); *C07C 2521/02* (2013.01); *C07C 2523/72* (2013.01); *C07C 2523/80* (2013.01); *C07C 2529/85* (2013.01); *C10G 2300/4006* (2013.01); *C10G 2300/4012* (2013.01)
(58) Field of Classification Search
  CPC ........ C07C 2523/80; C10G 2/33; C10G 2/50; C10G 2300/4012; C10G 2300/4006; B01J 23/80; B01J 29/85
  See application file for complete search history.

(56) References Cited

U.S. PATENT DOCUMENTS

| 7,405,337 B2 | 7/2008 | Kalnes et al. |
| 7,414,167 B2 | 8/2008 | Kalnes et al. |
| 2006/0063956 A1 | 3/2006 | Kalnes et al. |
| 2015/0232345 A1 | 8/2015 | Fan et al. |
| 2017/0210679 A1* | 7/2017 | Chojecki ............ C07C 1/12 |

OTHER PUBLICATIONS

Ye et al., "Synthesis Optimization of SAPO-34 in the Presence of Mixed Template for MTO Process," Adv. Matl. Research, 132 (2010) 246-256.
International Search Report and Written Opinion pertaining to PCT/US2018/016617, dated Apr. 30, 2018.

* cited by examiner

PROCESSES FOR IMPROVING THE ACTIVITY OF HYBRID CATALYSTS

CROSS REFERENCE TO RELATED APPLICATIONS

This application claims priority to U.S. Provisional Patent Application Ser. No. 62/454,954, filed Feb. 6, 2017, which is incorporated by reference herein in its entirety.

BACKGROUND

Field

The present specification generally relates to improving the activity of hybrid catalysts in the process of converting a feed stream comprising CO, $CO_2$, and combinations thereof to desired products. In particular, the present specification relates to improving the activity of a hybrid catalyst, which is used to convert synthesis gas into lightweight hydrocarbons, by modifying the pressure in a reaction zone that houses the hybrid catalyst.

Technical Background

For a number of industrial applications, desirable starting materials are light hydrocarbons, including in particular $C_2$ to $C_5$ olefins, and/or $C_2$ to $C_5$ paraffins that can then be converted to olefins, for use in or as starting materials to produce plastics, fuels, and various downstream chemicals. A variety of processes for producing these light hydrocarbons have been developed, including petroleum cracking and various synthetic processes.

Synthetic processes for converting feed streams comprising carbon to desired products, such as hydrocarbons, are known. Some of these synthetic processes use a hybrid catalyst to facilitate the conversion process. Different types of catalysts have also been explored, as well as different kinds of feed streams and proportions of feed stream components. However, many of these synthetic processes quickly deactivate the hybrid catalyst, which leads to more regeneration cycles that are costly and time-consuming.

Accordingly, a need exists for processes that improve the activity of hybrid catalysts used to convert carbon in carbon-containing feed streams, such as syngas, into light hydrocarbons.

SUMMARY

According to one embodiment, a process for converting a feed stream to $C_2$ to $C_5$ hydrocarbons, comprises: introducing a feed stream comprising hydrogen and at least one carbon-containing component selected from the group consisting of CO, $CO_2$, and mixtures thereof into a reaction zone at an initial reactor pressure and an initial reactor temperature; contacting the feed stream to a hybrid catalyst positioned in the reaction zone, wherein the hybrid catalyst comprises a methanol synthesis component and a solid microporous acid material; and increasing a pressure within the reaction zone during the contacting of the feed stream to the hybrid catalyst from the initial reactor pressure to a final reactor pressure, wherein a temperature within the reaction zone at any time during the contacting of the feed stream to the hybrid catalyst is within ±20° C. of the initial reactor temperature.

According to another embodiment, the pressure within the reaction zone during the contacting of the feed stream to the hybrid catalyst is increased from the initial reactor pressure to the final reactor pressure at a plurality of intervals. In some embodiments, the duration of each of the plurality of intervals may be at least 12 hours, and the pressure increase at each of the plurality of intervals may be at least 1 bar (0.1 MPa). In other embodiments, the duration of each of the plurality of intervals may be infinitesimally small and the pressure increase at each of the plurality of intervals may be infinitesimally small, such that the pressure increase is nearly continuous.

According to yet another embodiment, the pressure within the reaction zone during the contacting of the feed stream to the hybrid catalyst is increased when a percentage yield of desired products reaches a predetermined threshold value. The pressure may be increased by at least 1 bar (0.1 MPa) when a percentage yield of desired products reaches the predetermined threshold value.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Reference will now be made in detail to embodiments of processes for converting a carbon-containing feed stream to light hydrocarbons using a hybrid catalyst while increasing the lifetime of the hybrid catalyst, embodiments of which are outlined in FIG. 1. In one embodiment, a process for converting a feed stream to $C_2$ to $C_5$ hydrocarbons, comprises: introducing a feed stream comprising hydrogen and at least one carbon-containing component selected from the group consisting of CO, $CO_2$, and mixtures thereof into a reaction zone at an initial reactor pressure and an initial reactor temperature; contacting the feed stream to a hybrid catalyst positioned in the reaction zone, wherein the hybrid catalyst comprises a methanol synthesis component and a solid microporous acid material; and increasing a pressure within the reaction zone during the contacting of the feed stream to the hybrid catalyst from the initial reactor pressure to a final reactor pressure, wherein a temperature within the reaction zone at any time during the contacting of the feed stream to the hybrid catalyst is within ±20° C. of the initial reactor temperature.

In conventional carbon conversion processes, the lifetime of a hybrid catalyst can be relatively short. As used herein the lifetime of the hybrid catalyst is defined as run time of a conversion process to the point where a yield of $C_2$ to $C_5$ hydrocarbons, such as $C_2$ to $C_5$ olefins and/or paraffins (in percentage) drops below a pre-determined threshold value. This percentage yield is based on the content of carbon in the feed stream that is converted to $C_2$ to $C_5$ hydrocarbons. Thus, a percentage yield of 50% would mean that 50% of the carbon in the feed stream is converted to $C_2$ to $C_5$ hydrocarbons. If the conversion process is left unaltered, the yield of $C_2$ to $C_5$ hydrocarbons can drop below 20% in less than 80 hours. Accordingly, there have been attempts to improve the activity of the catalyst during various carbon conversion processes. For instance, in conventional methanol synthesis processes having a catalyst, both the temperature and the pressure within the reaction zone comprising the catalyst are increased substantially simultaneously. It is believed that these substantially simultaneous increases in temperature and pressure during the conversion process compensates for loss of activity through the lifetime of a catalyst charge. Similarly, in methanol-to-propylene conversion processes, it was conventionally believed that activity loss due to coke deposition on the catalyst could be compensated for by increasing the temperature in the reaction zone. See, e.g., U.S. Patent Publication No. 2006/0063956, U.S. Pat. Nos. 7,414,167, and 7,405,337. However, it was thought that increasing the pressure in methanol-to-propylene conversion processes would reduce the output of desired products. For instance, it is known that light hydrocarbons, such as, for example, propylene and the like, are formed under low pressure conditions, such as from 1 to 3 atm (101 to 304 kPa). Accordingly, it was not previously thought that increasing only the pressure (i.e., without increasing the temperature) in carbon conversion process would increase the lifetime of a catalyst.

However, as described in embodiments of processes disclosed herein, it has been found that increasing only the pressure within the reaction zone comprising the hybrid catalyst is more effective at maintaining the activity of a hybrid catalyst when converting a carbon-containing feed stream to $C_2$ to $C_5$ hydrocarbons.

Figure 1:
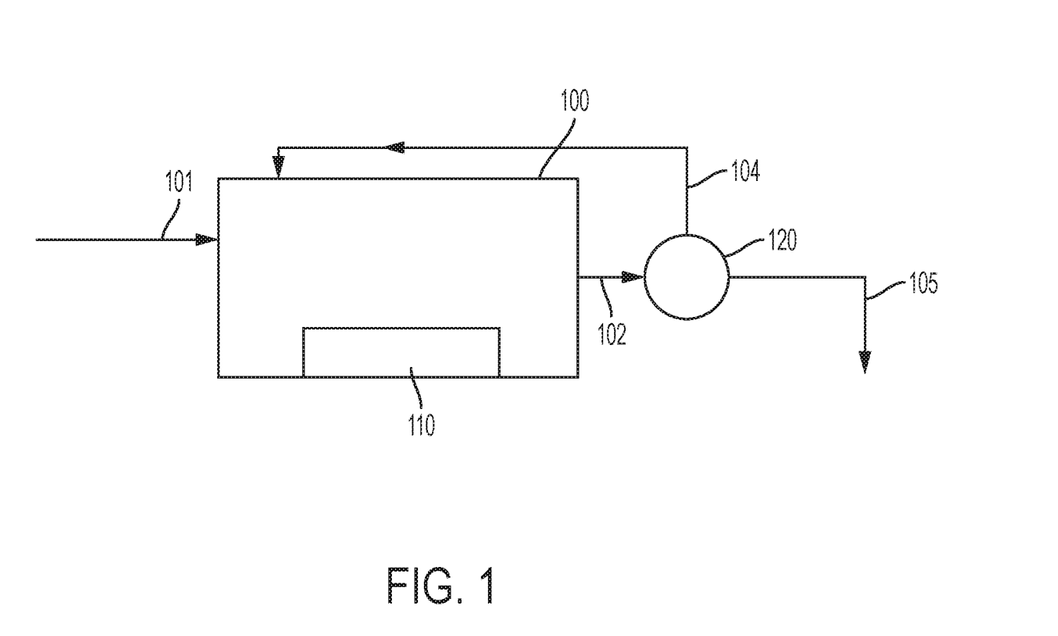
FIG. 1 is a schematic diagram of processes for improving the activity of a hybrid catalyst according to embodiments disclosed and described herein.

With reference now to FIG. 1, processes according to embodiments comprise a feed stream 101, a reaction zone 100 comprising a hybrid catalyst 110, and an outlet stream 102. In addition to the reaction zone 100, a separator 120 may be used to separate unconverted carbon and other non-product components from the outlet stream 102 into a recycle stream 104 and a final product stream 105.

The feed stream 101 is introduced into the reaction zone 100 that comprises the hybrid catalyst 110. According to some embodiments, the feed stream 101 comprises hydrogen ($H_2$) and at least one carbon-containing component. In certain embodiments, the carbon-containing component may be carbon monoxide (CO), carbon dioxide ($CO_2$), and combinations thereof. The content of $H_2$ in the feed stream 101 in various embodiments may be from 50 volume percent (vol %) to 80 vol %, such as from 55 vol % to 75 vol %, or from 60 vol % to 70 vol %. The remainder (i.e., the components other than $H_2$) of the feed stream 101 comprises primarily CO. Accordingly, the feed stream 101 may comprise CO in amounts from 20 vol % to 50 vol %, such as from 25 vol % to 45 vol %, or from 30 vol % to 40 vol %. The volumetric ratio of $H_2$ to CO in the feed stream 101 may be from 1:1 to 4:1, such as from 1.5:1 to 3.5:1, or from 2:1 to 3:1, according to embodiments. As will be recognized by those skilled in the art, there is often one or more additional components that may be present in small amounts in the feed stream 101, including in particular carbon dioxide ($CO_2$), inert gases (such as nitrogen ($N_2$)), additional carbon-containing compounds, such as methane ($CH_4$), another hydrocarbon, such as a small amount of ethane ($C_2H_6$) or ethylene ($C_2H_4$), or combinations of the foregoing. The feed stream 101 is, in certain embodiments, syngas. However, it should be understood that the feed stream 101 may be any stream that comprises $H_2$ and at least one carbon-containing component.

Subsequent to being introduced into the reaction zone 100, the feed stream flows on or through the hybrid catalyst 110, which is present within the reaction zone 100. In embodiments, the hybrid catalyst 110 comprises, consists of, or consists essentially of (1) a methanol synthesis component; and (2) a solid microporous acid component having 8 membered ring (MR) access to 12 MR access. In some embodiments, the solid microporous acid component has 8 MR access.

The methanol synthesis component can be a metal oxide or mixed metal oxide or supported metal oxide or supported mixed metal oxide capable of converting the feed stream into methanol or DME under hybrid process conditions. In some embodiments, the methanol synthesis component may be selected from the group consisting of a copper oxide catalyst, a copper oxide/zinc oxide catalyst, a copper oxide/alumina catalyst, a copper oxide/zinc oxide/alumina catalyst, a chromium oxide/zinc oxide catalyst, and combinations thereof.

In embodiments, the methanol synthesis component may comprise one or more of the elements Cu, Zn, Cr, and Al, in any possible compositional combination and in either metallic or oxidic form.

It is additionally noted that the aluminum oxide (i.e., alumina) may be in any phase or combination of phases. However, in some embodiments a gamma-alumina, or predominantly (more than 50 wt %) of gamma-alumina, the weight percent being based on total alumina may be used. Other phases of aluminas, such as alpha-alumina, omega-alumina, eta-alumina, etc., may be used alternatively or as a component, such as a minor component, with another alumina phase, such as a gamma phase.

In further embodiments, the methanol synthesis component, once formulated, may be calcined to form a metal oxide that can be used in the hybrid catalyst as the methanol synthesis component. The calcination temperature in some embodiments may be from 300° C. to 500° C., from 325° C. to 475° C., from 350° C. to 450° C., from 375° C. to 425° C., or about 400° C.

In embodiments, the solid microporous acid component is selected from molecular sieves having 8-MR access to limit the size distribution of products and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be silicoaluminophosphate having a CHA framework type. Examples of these may include, but are not necessarily limited to: CHA embodiments selected from SAPO-34 and SSZ-13; and AEI embodiments such as SAPO-18. As the term is used herein, "SAPO" molecular sieves are defined as silicoaluminophosphate materials having a silicon content of at least 0.01 wt %, such as at least 0.1 wt %, and at least 0.5 wt %. Many of these materials will have a silicon content of at least 5 wt % or greater. Thus, based upon this definition, molecular sieves that are primarily aluminophosphates, but actually contain very minor amounts of silicon (i.e., less than 0.01 wt %, would still be classified as "ALPO" molecular sieves). In other embodiments the molecular sieve may be ZSM-5 aluminosilicate having an MFI framework type. As the term is used herein, "ZSM-5" molecular sieves are defined as aluminosilicate materials having an aluminum content of at least 0.01 wt %, such as at least 0.1 wt %, and at least 0.5 wt %. Combinations of molecular sieves having any of the above framework types may also be employed. It should be understood that the solid microporous acid component may have different membered ring access depending on the desired product. For instance, solid microporous acid components having 8-MR to 12-MR access could be used depending on the desired product. However, to produce $C_2$ to $C_5$ hydrocarbons, solid microporous acid components having 8-MR access are used in embodiments.

In some embodiments, the SAPO-34 may be used in its acid form. Those skilled in the art will understand that in its acid form the cations charge balancing the framework consists predominantly of proton ions ($H^+$). In other embodiments some fraction of the $H^+$ ions can be substituted with other ions, for example, those of the alkaline or alkali group of metals, or other metals such as, for example, copper, chromium or zinc from the methanol synthesis component.

The SAPO-34 component may be prepared, prior to combining it with the methanol synthesis component, via a templating method that is well-known to those skilled in the art. See, e.g., U.S. Patent Application Publication 2015/0232345; G. Liu, et al., "Synthesis of SAPO-34 templated by diethylamine: Crystallization process and Si distribution in the crystals," *Microporous and Mesoporous Materials*, 114 (2008) 1-3, 416-423; Online publication of International Zeolite Association www.iza-online.org/synthesis/-Recipes/SAPO-34.html (includes XRD pattern); and/or L. P. Ye, et al., "Synthesis Optimization of SAPO-34 in the Presence of Mixed Template for MTO Process," *Adv. Mad. Research*, 132 (2010) 246-256.

As it is known to those skilled in the art, after preparation and before use, SAPO-34 may be calcined to remove at least a portion of the templating agent. See, for example, U.S. Pat. No. 4,440,871. The calcination may be accomplished by placing SAPO-34 in an oxygen-containing gas stream, such as, for example, air and gradually increasing the temperature to a temperature effective for removing at least a portion of the templating agent. Generally, this temperature is between 200° C. and 700° C., such as, for example, 600° C. The SAPO-34 may then be held at that temperature for a time period sufficient to remove the templating agent, such as, for example, from 1 to 24 hours. In some embodiments, the SAPO-34 may be held at this temperature for about 4 hours.

Once the two components—the methanol synthesis component and the solid microporous acid component—have been prepared, they may be mixed together using any means and methods generally known to those skilled in the art to maximize distribution of the components within the hybrid catalyst, thereby theoretically optimizing their joint effect on any given volume of feed stream. In embodiments the components are combined in proportion such that, in the reactor bed (whether fixed, moving and/or fluidized), they have a weight/weight (wt/wt) ratio of methanol synthesis component(s):solid microporous acid component(s) ranging from 0.1:1 to 10:1, such as from 0.5:1 to 8:1, or from 1:1 to 5:1. After the two components have been mixed, the mixture is packed into the reactor bed where the feed stream 101 is introduced to the hybrid catalyst 110.

In some embodiments, the hybrid catalyst may be reduced before the feed stream 101 is flowed into the reaction zone 100. This may be done by introducing a hydrogen-containing stream into the reaction zone 100 and flowing the hydrogen-containing stream over the hybrid catalyst 110. In some embodiments, the hybrid catalyst 110 is reduced by introducing hydrogen at a gas hourly space velocity (GHSV) from 1000 $hr^{-1}$ to 4000 $hr^{-1}$, such as from 2000 $hr^{-1}$ to 3500 $hr^{-1}$, or about 3000 $hr^{-1}$. In embodiments, to reduce the hybrid catalyst 110, the temperature in the reaction zone 100 is from 200° C. to 400° C., such as from 250° C. to 300° C., or about 270° C., and the pressure in the reaction zone is from ambient (e.g., 1 bar (0.1 MPa)) to 15 bars (1.5 MPa, such as from 8 bars (0.8 MPa) to 12 bars (1.2 MPa), or about 10 bars (1.0 MPa). The reduction process may take place for a duration of from 1 hour to 24 hours, such as about 6 hours.

In other embodiments, the hybrid catalyst 110 is reduced in process by flowing the feed stream 101 over the hybrid catalyst 110. This reduction takes place at the reaction conditions discussed below.

As stated above, the feed stream 101 flows on or through the hybrid catalyst 110. During this contacting of the feed stream 101 to the hybrid catalyst 110, the reaction conditions within the reaction zone 100 should be sufficient to convert at least a portion of the carbon-containing gas in the feed stream 101 into a product mixture. The conditions under which this process may be carried out comprise, consist essentially of, or consist of: (1) a reactor temperature ranging from 350° C. to 450° C., such as from 375° C. to 425° C., or from 385° C. to 415° C.; and (2) an initial reactor pressure of at least 15 bar (1.5 MPa). According to embodiments, the final reactor pressure is at least 1 bar (0.1 MPa) greater than the initial reactor pressure and a maximum pressure is about 120 bar (12 MPa). In some embodiments it is also desirable, for reasons of acceptable industrial productivity, for the feed stream's gas hourly space velocity (GHSV) to be greater than 500 reciprocal hours ($h^{-1}$).

As used hereinabove, the phrase "reactor temperature" will be understood to represent either an average reactor temperature, where temperature is measured at more than one location within the reactor, or the sole temperature, where temperature is measured at only one location within the reactor. However, those skilled in the art will recognize that the temperature at different locations within the reactor will almost certainly vary somewhat, according to feed stream component flow rates, catalyst flow where moving/fluidized bed reactors are employed, bed packing, reactor size and geometry, variations in reactor inlet temperatures, and so forth, and will be able to easily adjust process parameters and other means to control the reactor temperature, to ensure that the reactor temperature requirements of embodiments are met. In addition to making modifications of the reaction parameters listed hereinabove, those skilled in the art may also design a given system such that additional and/or alternative means of temperature control, such as the use of a multi-tube heat exchanger, may be employed. Similarly, "initial reactor pressure" and "final reactor pressure as used herein will be understood to represent an average initial reactor pressure or average final reactor pressure, where the pressure is measured at more than one location within the reactor, or the sole initial reactor pressure or final reactor pressure, where the pressure is measured at only one location within the reactor. However, those skilled in the art will recognize that the pressure at different locations within the reactor will almost certainly vary somewhat according to feed stream flow rates, outlet stream flow rates, catalyst flows where moving/fluidized bed reactors are employed, bed packing, and so forth and will be able to easily adjust process parameters and other means to control the initial reactor pressure and the final reactor pressure, to ensure that the reactor pressure requirements of embodiments are met. In addition to making modifications of the reaction parameters listed hereinabove, those skilled in the art may also design a given system such that additional and/or alternative means of pressure control, such as the use of pumps and the like, may be employed.

In certain embodiments, such reaction conditions comprise, consist essentially of, or consist of: (1) a reactor temperature ranging from greater than 350° C., such as greater than 360° C., greater than 380° C., or greater than 390° C. to less than 450° C., such as less than 430° C., less than 420° C., or less than 410° C.; (2) an initial reactor pressure of at least 15 bar (1.5 MPa), at least 16 bar (1.6 MPa), or at least 17 bar (1.7 MPa), the final reactor pressure is at least 1 bar (0.1 MPa) greater than the initial pressure, at least 5 bar (0.5 MPa) greater than the initial pressure, or at least 10 bar (1.0 MPa) greater than the initial pressure with a maximum pressure of about 120 bar (12 MPa); and (3) a GHSV of greater than 500 $h^{-1}$, such as greater than 800 $h^{-1}$, or greater than 1,000 $h^{-1}$, to less than 12,000 $h^{-1}$, such as less than 10,000 $h^{-1}$, or less than 8,000 $h^{-1}$. In some embodiments, the reaction zone 100 may be pre-pressurized to the initial reactor pressure before the feed stream 101 is introduced into the reaction zone 100. In other embodiments, the feed stream 101 is introduced into the reaction zone 100 while the pressure within the reaction zone 100 is being raised to the initial reactor pressure.

As noted above, the activity of the hybrid catalyst decreases as the conversion of feed stream to desirable products proceeds. This decreased activity is reflected in a decreased percentage yield of desired products, such as $C_2$ to $C_5$ hydrocarbons, in the outlet stream 102. For instance, in embodiments, the initial percentage yield of $C_2$ to $C_5$ hydrocarbons in the outlet stream 102 is greater than 20%, such as greater than 25%, or greater than 30%. As stated above, the percentage yield is based on the amount of carbon in the feed stream 101, thus a percentage yield of 20% converts 20% of the carbon in the feed stream to $C_2$ to $C_5$ hydrocarbons. However, during the conversion process, the yield of the desired products (e.g., $C_2$ to $C_5$ hydrocarbons) decreases relatively quickly without intervention. Without being bound to any particular theory, this reduction in activity is believed to be caused by the deactivation of the methanol synthesis component of the hybrid catalyst. To address this issue, processes according to embodiments increase the pressure within the reaction zone during the conversion process without significantly increasing the temperature within the reaction zone, which improves the activity of the hybrid catalyst during the conversion process. Accordingly, the final reactor pressure within the reaction zone will be greater than the initial reactor pressure. As used herein, the "final reactor pressure" refers to the maximum pressure within the reaction zone before the feed stream is shut off and the hybrid catalyst is regenerated or retired.

In embodiments, the final reactor pressure is at least 1 bar (0.1 MPa) greater than the initial reactor pressure, such as at least 5 bar (0.5 MPa) greater than the initial reactor pressure, at least 10 bar (1.0 MPa) greater than the initial reactor pressure, at least 15 bar (1.5 MPa) greater than the initial reactor pressure, at least 20 bar (2.0 MPa) greater than the initial reactor pressure, at least 25 bar (2.5 MPa) greater than the initial reactor pressure, at least 30 bar (3.0 MPa) greater than the initial reactor pressure, at least 35 bar (3.5 MPa) greater than the initial reactor pressure, at least 40 bar (4.0 MPa) greater than the initial reactor pressure, at least 45 bar (4.5 MPa) greater than the initial reactor pressure, at least 50 bar (5.0 MPa) greater than the initial reactor pressure, at least 55 bar (5.5 MPa) greater than the initial reactor pressure, or at least 60 bar (6.0 MPa) greater than the initial reactor pressure. It should be understood that the final reactor pressure is limited by the desired reaction conditions and equipment. Accordingly, in various embodiments, the final reactor pressure may be from 16 bar (1.6 MPa) to 120 bar (12 MPa), such as from 20 bar (2.0 MPa) to 100 bar (10 MPa), such as from 25 bar (2.5 MPa) to 75 bar (7.5 MPa), from 35 bar (3.5 MPa) to 65 bar (6.5 MPa), from 40 bar (4.0 MPa) to 60 bar (6.0 MPa), or from 45 bar (4.5 MPa) to 55 bar (5.5 MPa).

The pressure within the reaction zone 100 may be increased at any suitable interval as the conversion process requires. In some embodiments, the pressure within the reaction zone 100 may be increased at specific time intervals. For example, the pressure within the reaction zone may be increased every 12 hours, every 18 hours, every 24 hours, every 30 hours, every 36 hours, every 42 hours, or every 48 hours of the conversion process. It should be understood that the interval at which the pressure within the reaction zone 100 is increased is not limited and will depend on specific reaction conditions and the desired yield of products. Accordingly, each interval may have the same duration, or any individual interval may have the same or different duration from any other interval. At each interval, the pressure within the reaction zone may be increased by any suitable amount as dictated by the reaction conditions and the desired yield of the products. In some embodiments, the pressure within the reaction zone 100 is increased by at least 1 bar (0.1 MPa) every interval, such as at least 5 bar (0.5 MPa) every interval, at least 7 bar (0.7 MPa) every interval, at least 10 bar (1.0 MPa) every interval, at least 15 bar (1.5 MPa) every interval, at least 20 bar (2.0 MPa) every interval, at least 25 bar (2.5 MPa) every interval, at least 30 bar (3.0 MPa) every interval, at least 35 bar (3.5 MPa) every interval, at least 40 bar (4.0 MPa) every interval, at least 45 bar (4.5 MPa) every interval, at least 50 bar (5.0 MPa) every interval, at least 55 bar (5.5 MPa) every interval, or about 60 bar (6.0 MPa) every interval. The pressure increase within the reaction zone 100 may be the same at each interval, or a pressure increase at any individual interval may be the same as or different from a pressure increase at any other interval.

In alternative embodiments, the duration of each of the intervals may be infinitesimally small, such that the pressure is essentially increasing continuously throughout the conversion process. In such embodiments, the pressure increase at each interval may be 1 bar (0.1 MPa) or less, such as 0.5 bars (0.05 MPa) or less, or 0.1 bar (0.01 MPa) or less. In certain embodiments, the pressure increase at each interval is infinitesimally small. It should be understood that the pressure increase at intervals having an infinitesimally small duration is limited by the process and equipments ability to increase the pressure within the reaction zone 100.

In other embodiments, the pressure within the reaction zone 100 may be increased when the percentage yield of the desired product reaches a predetermined threshold value. The predetermined threshold value is not limited and will depend on the desired output of certain products. In embodiments, the predetermined threshold value is based on the percentage yield of $C_2$ to $C_5$ hydrocarbons and may be greater than 20% $C_2$ to $C_5$ hydrocarbon yield, such as greater than 25% $C_2$ to $C_5$ hydrocarbon yield, greater than 30% $C_2$ to $C_5$ hydrocarbon yield, greater than 35% $C_2$ to $C_5$ hydrocarbon yield, greater than 40% $C_2$ to $C_5$ hydrocarbon yield, greater than 45% $C_2$ to $C_5$ hydrocarbon yield, greater than 50% $C_2$ to $C_5$ hydrocarbon yield, greater than 55% $C_2$ to $C_5$ hydrocarbon yield, or greater than 60% $C_2$ to $C_5$ hydrocarbon yield. As stated above, the yield of desired products generally decreases as the conversion process proceeds. Thus, the yield of desired products, such as, for example, $C_2$ to $C_5$ hydrocarbons, in the outlet stream 102 may be monitored and, when the yield of desired products decreases to the predetermined threshold value, the pressure within the reaction zone 100 is increased to cause a corresponding increase in the percentage yield of desired products. From the above, it should be understood that, in embodiments, the predetermined threshold value should be set above the minimum desired yield so that the pressure increase within the reaction zone 100 has time to increase the desired product yield before the yield drops below the minimum desired yield. In embodiments, the predetermined threshold value may be 2 percentage yield above the minimum desired yield, such as 5 percentage yield above the minimum desired yield, 7 percentage yield above the minimum desired yield, or 10 percentage yield above the minimum desired yield. The pressure increase within the reaction zone 100 at the predetermined threshold value is not limited and will depend on the desired reaction conditions and the responsiveness of the desired product yield to the increase in pressure. In embodiments, the pressure within the reaction zone 100 is increased by at least 1 bar (0.1 MPa) when the predetermined threshold value is reached, such as at least 5 bar (0.5 MPa) when the predetermined threshold value is reached, at least 7 bar (0.7 MPa) when the predetermined threshold value is reached, at least 10 bar (1.0 MPa) when the predetermined threshold value is reached, at least 15 bar (1.5 MPa) when the predetermined threshold value is reached, at least 20 bar (2.0 MPa) when the predetermined threshold value is reached, at least 25 bar (2.5 MPa) when the predetermined threshold value is reached, at least 30 bar (3.0 MPa) when the predetermined threshold value is reached, at least 35 bar (3.5 MPa) when the predetermined threshold value is reached, at least 40 bar (4.0 MPa) when the predetermined threshold value is reached, at least 45 bar (4.5 MPa) when the predetermined threshold value is reached, at least 50 bar (5.0 MPa) when the predetermined threshold value is reached, at least 55 bar (5.5 MPa) when the predetermined threshold value is reached, at least 20 bar (2.0 MPa) when the predetermined threshold value is reached, or about 60 bar (6.0 MPa) when the predetermined threshold value is reached.

In any of the above embodiments, the pressure within the reaction zone 100 may be increased by conventional pressure modifications methods known to one of ordinary skill in the art, such as, for example, increasing the flow rate of the feed stream 101, decreasing the flow rate of the outlet stream 102, a combination of increasing the flow rate of the feed stream 101 and decreasing the flow rate of the outlet stream 102, or by conventional pressure modification equipment, such as, for example pumps, valves, compressors, and the like.

As stated above, while the pressure within the reaction zone 100 is increased, the temperature within the reaction zone is kept substantially constant. However, variations of the temperature within the reaction zone may occur during the conversion process as the pressure within the reaction zone is increased and as reactions proceed. In embodiments, these variations in temperature are minimized so that the temperature within the reaction zone 100 at any time during the conversion process is within ±20° C. of the initial reactor temperature, such as within ±15° C. of the initial reactor temperature, within ±10° C. of the initial reactor temperature, or within ±5° C. of the initial reactor temperature. The temperature within the reaction zone 100 may be controlled by conventional temperature control methods known to one of ordinary skill in the art, such as active cooling via a cooling loop, active air cooling, and the like.

After the feed stream 101 is introduced to the hybrid catalyst 110 in the reaction zone 100 and at least a portion of the feed stream 101 is converted into a desired product, such as $C_2$ to $C_5$ hydrocarbons, the product exits the reaction zone 100 via an outlet stream 102. The outlet stream 102 will, as will be understood by one of ordinary skill in the art, contain proportions of the desired product, such as $C_2$ to $C_5$ hydrocarbons, and the unconverted feed stream gases, as well as, typically, water resulting from the reactions which take place. The amount of each will vary according to a variety of factors well known to those skilled in the art, including carbon conversion, yield, catalyst productivity, time on stream, and so forth. The unconverted feed stream gases may be separated from the product mixture in the separator 120 and, if desired, recycled back into the process as recycle stream 104. The desired product exits the separator 120 as a final product stream 105. Alternatively, the recycle stream 104 may be disposed of in an environmentally approved and responsible manner, as will be well-known to those skilled in the art. The separator 120 is not particularly limited and can be any suitable separator known to one of ordinary skill in the art. The final product stream 105 can then be used as or in starting materials for various chemical forming processes.

EXAMPLES

Embodiments will be further clarified by the following examples.

Example 1

Example 1 shows the effect that pressure has on the activity of a hybrid catalyst comprising a copper-zinc-aluminum methanol synthesis component and SAPO-34 as the solid microporous acid component. Initially, the SAPO-34 was formulated by stirring together 8.2 grams of aluminum isopropoxide ($Al(OC_3H_7)_3$) with a solution of 3.9 grams of 85 wt % orthophosphoric acid in 8.4 grams of water. Subsequently, 1.2 grams of an aqueous sol of 30 wt % $SiO_2$ (Ludox AS-30) and 0.5 grams of water were stirred into the mixture until the resultant was homogeneous. Finally, 16.8 grams of an aqueous solution of 35 wt % tetraethylammonium hydroxide (TEAOH) was added to the mixture to form the reaction mixture.

Once formulated, the reaction mixture was placed in a stainless steel stirred Parr reactor and heated to 200° C. at 0.5° C./min. The temperature was maintained for 120 hours under autogenous pressure while stirring at 60 RPM. The product was recovered by centrifugation, washed with water and dried at 90° C. overnight.

A portion of the recovered product required for catalytic testing was calcined in a muffle furnace in air to remove the templating agent. This was accomplished by gradually increasing the temperature in the furnace to 600° C. at a heating rate of 2° C./min, and holding at 600° C. for a period of 4 hours. This calcined material was used in the subsequent samples and examples as the SAPO-34 component.

Once the SAPO-34 was formulated, 0.50 grams of the SAPO-34 was physically mixed with 1 gram of a copper-zinc-aluminum mixed metal oxide catalyst (HiFUEL™ R120, Alfa Aesar™, a Johnson Matthey Company) by shaking them together in a bottle. Each of the catalysts had a particle size before mixing within a range of from 40 mesh (0.422 mm) to 80 mesh (0.178 mm). The physically mixed catalyst was activated using a pure hydrogen stream at a flow rate of 100 ml/min, a temperature of 270° C., and a pressure of 10 bars (1.0 MPa) for a period of 6 hours. The system was pressurized with pure nitrogen up to 35 bar (3.5 MPa). Subsequently, the system was heated to 400° C. while still flowing pure nitrogen. Then, 22.5 ml/min CO, 67.5 ml/min $H_2$ and 10 ml/min He was passed over the catalyst. While the stream was passed over the catalyst, the pressure at the catalyst was increased in steps of 5 bar (0.5 MPa) every 48 hours up to 45 bar (4.5 MPa). The temperature was kept at about 400° C. (e.g., 400° C.±0.2° C.

Figure 2:
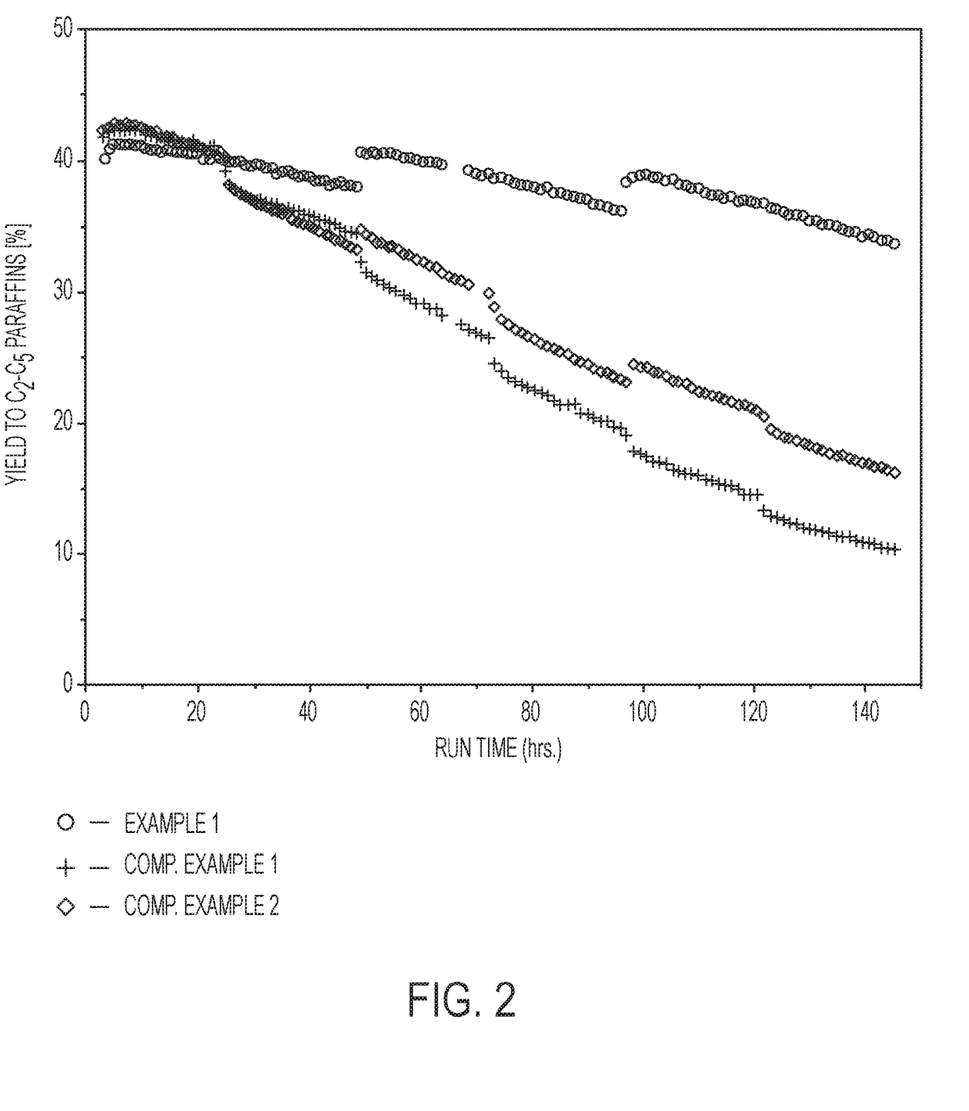
FIG. 2 is a scatter chart showing the yield of $C_2$ to $C_5$ paraffins versus the runtime of comparative processes and a process according to embodiments disclosed and described herein.

As can be seen in FIG. 2, the activity of the hybrid catalyst is increased at each point where the pressure is increased, as indicated by a bump in the percentage yield of $C_2$ to $C_5$ paraffins when the pressure is increased. Using these 5 bar (0.5 MPa) pressure increases every 48 hours allows the percentage yield of $C_2$ to $C_5$ paraffins to be maintained above 30%. Thus, this example shows the effect that increasing only the pressure has on the percentage yield of the desired product.

Comparative Example 1

SAPO-34 was prepared as described above in Example 1. Once formulated, 0.50 grams of SAPO-34 was physically mixed with 1 gram of a copper-zinc-aluminum mixed metal oxide catalyst (HiFUEL™ R120, Alfa Aesar™, a Johnson Matthey Company) by shaking them together in a bottle. Each of the catalysts had a particle size before mixing within a range of from 40 mesh (0.422 mm) to 80 mesh (0.178 mm). The physically mixed catalyst was activated using a pure hydrogen stream at a flow of 100 ml/min, a temperature of 270° C., and a pressure of 10 bars (1.0 MPa) for a period of 6 hours. Subsequently, the system was heated to 400° C. while flowing pure nitrogen. The system was pressurized with pure nitrogen up to 35 bar (3.5 MPa). Then, 22.5 ml/min CO, 67.5 ml/min $H_2$ and 10 ml/min He was passed over the catalyst. While the stream was passed over the catalyst, the temperature was increased in steps of 10° C. every 24 hours up to 450° C.

As can be seen in FIG. 2, the activity of the hybrid catalyst unexpectedly decreases when the temperature is increased. This is indicated by drops in the percentage yield of $C_2$ to $C_5$ paraffins when the temperature is increased. In this example, the percentage yield of $C_2$ to $C_5$ paraffins was not maintained above 20%.

Comparative Example 2

SAPO-34 was prepared as described above in Example 1. Once formulated, 0.50 grams of SAPO-34 was physically mixed with 1 gram of a copper-zinc-aluminum mixed metal oxide catalyst (HiFUEL™ R120, Alfa Aesar™, a Johnson Matthey Company) by shaking them together in a bottle. Each of the catalysts had a particle size before mixing within a range of from 40 mesh (0.422 mm) to 80 mesh (0.178 mm). The physically mixed catalyst was activated using a pure hydrogen stream at a flow of 100 ml/min, a temperature of 270° C., and a pressure of 10 bars (1.0 MPa) for a period of 6 hours. Subsequently, the system was heated to 400° C. while flowing pure nitrogen. The system was pressurized with pure nitrogen up to 35 bar (3.5 MPa). Then, 22.5 ml/min CO, 67.5 ml/min $H_2$ and 10 ml/min He was passed over the catalyst. While the stream was passed over the catalyst, the pressure was increased in steps of 5 bar (0.5 MPa) every 48 hours up to 45 bar (4.5 MPa) and the temperature was increased in steps of 10° C. every 24 hours up to 450° C.

As can be seen in FIG. 2, the activity of the hybrid catalyst unexpectedly decreases when the temperature and pressure is increased. This is indicated by drops in the percentage yield of $C_2$ to $C_5$ paraffins when the temperature is increased. Although there may be a slight initial improvement in percentage yield caused by the increase in pressure, this improvement is offset by the increase in temperature. In this example, the percentage yield of $C_2$ to $C_5$ paraffins was not maintained above 20%.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A process for converting a feed stream to $C_2$ to $C_5$ hydrocarbons, comprising:
    introducing a feed stream comprising hydrogen and at least one carbon-containing component selected from the group consisting of CO, $CO_2$, and mixtures thereof into a reaction zone at an initial reactor pressure and an initial reactor temperature;
    contacting the feed stream to a hybrid catalyst positioned in the reaction zone, wherein the hybrid catalyst comprises a methanol synthesis component and a solid microporous acid material; and
    increasing a pressure within the reaction zone during the contacting of the feed stream to the hybrid catalyst from the initial reactor pressure to a final reactor pressure,
    wherein a temperature within the reaction zone at any time during the contacting of the feed stream to the hybrid catalyst is within ±20° C. of the initial reactor temperature.

2. The process of claim 1, wherein the final reactor pressure is at least 1 bar (0.1 MPa) greater than the initial reactor pressure.

3. The process of claim 1, wherein the final reactor pressure and is from 1 bar (0.1 MPa) to 60 bar (6.0 MPa) greater than the initial reactor pressure.

4. The process of claim 1, wherein the initial reactor pressure is from 15 bar (1.5 MPa) to 60 bar (6.0 MPa) and the final reactor pressure is from 16 bar (1.6 MPa) to 120 bar (12.0 MPa).

5. The process of claim 1, wherein the initial reactor temperature is from 350° C. to 450° C.

6. The process of claim 1, wherein a temperature within the reaction zone at any time during the contacting of the feed stream to the hybrid catalyst is within ±10° C. of the initial reactor temperature.

7. The process of claim 1, wherein
    the methanol synthesis component comprises one or more of Cu, Zn, Cr, and Al in any possible compositional combination and in either metallic or oxidic form, and
    the solid microporous acid material is selected from molecular sieves having 8-MR access and having a framework type selected from the group consisting of framework types CHA, AEI, AFX, ERI, LTA, UFI, RTH, and combinations thereof, the framework types corresponding to the naming convention of the International Zeolite Association.

8. The process of claim 1, wherein a flow rate of the feed stream is greater than 500 reciprocal hours ($h^{-1}$).

9. The process of claim 1, wherein the pressure within the reaction zone during the contacting of the feed stream to the hybrid catalyst is increased from the initial reactor pressure to the final reactor pressure at a plurality of intervals.

10. The process of claim 9, wherein a duration of each of the plurality of intervals is at least 12 hours.

11. The process of claim 9, wherein a pressure increase at each of the plurality of intervals is at least 1 bar (0.1 MPa).

12. The process of claim 9, wherein a duration of each of the plurality of intervals is from 12 hours to 48 hours, and a pressure increase at each of the plurality of intervals is at least 1 bar (0.1 MPa).

13. The process of claim 1, wherein the pressure within the reaction zone during the contacting of the feed stream to the hybrid catalyst is increased when a percentage yield of desired products reaches a predetermined threshold value.

14. The process of claim 13, wherein a pressure within the reaction zone is increased by at least 1 bar (0.1 MPa) when the percentage yield of desired products reaches the predetermined threshold value.

15. The process of claim 13, wherein a pressure within the reaction zone is increased by at least 5 bar (0.5 MPa) when the percentage yield of desired products reaches the predetermined threshold value.

* * * * *